United States Patent [19]
Armini

[11] Patent Number: 6,060,036
[45] Date of Patent: May 9, 2000

[54] RADIOACTIVE SEED IMPLANTS

[75] Inventor: Anthony J. Armini, Wakefield, Mass.

[73] Assignee: Implant Sciences Corporation, Wakefield, Mass.

[21] Appl. No.: 09/047,728

[22] Filed: Mar. 25, 1998

Related U.S. Application Data

[60] Provisional application No. 60/074,085, Feb. 9, 1998.
[51] Int. Cl.[7] .......................... A61K 51/00; A61M 36/14
[52] U.S. Cl. .............................. 424/1.29; 424/422; 600/3; 600/7; 600/2
[58] Field of Search ................................. 424/1.11, 1.29, 424/1.37, 9.1, 9.3, 9.4, 9.5, 9.6, 9.7, 422; 600/1–8; 206/528; 604/890.1, 891.2, 891.1

[56] References Cited

U.S. PATENT DOCUMENTS

| | | | |
|---|---|---|---|
| Re. 29,066 | 12/1976 | Evans ........................................... | 424/1 |
| 1,718,899 | 6/1929 | Fischer . | |
| 3,351,049 | 11/1967 | Lawrence . | |
| 3,663,385 | 5/1972 | Evans ........................................... | 424/1 |
| 3,750,653 | 8/1973 | Simon ....................................... | 128/1.2 |
| 4,101,646 | 7/1978 | Sugimoto ................................... | 424/4 |
| 4,323,055 | 4/1982 | Kubiatowicz ............................. | 128/1.2 |
| 4,398,089 | 8/1983 | Sharpe .................................. | 250/336.1 |
| 4,510,924 | 4/1985 | Gray ........................................ | 128/1.2 |
| 4,584,991 | 4/1986 | Tokita et al. .............................. | 128/1.1 |
| 4,586,490 | 5/1986 | Katz ......................................... | 128/1.1 |
| 4,660,547 | 4/1987 | Kremer, Jr. ............................... | 128/1.1 |
| 4,697,575 | 10/1987 | Horowitz ................................. | 128/1.2 |
| 4,702,228 | 10/1987 | Russell, Jr. et al. ...................... | 128/1.2 |
| 4,714,074 | 12/1987 | Rey et al. ................................. | 128/1.1 |
| 4,715,359 | 12/1987 | Ryo ......................................... | 128/1.1 |
| 4,733,653 | 3/1988 | Leung et al. ............................. | 128/1.2 |
| 4,784,116 | 11/1988 | Russell, Jr. et al. ...................... | 128/1.2 |
| 4,803,977 | 2/1989 | Kremer, Jr. ................................. | 600/3 |
| 4,815,446 | 3/1989 | McIntosh .................................... | 600/3 |
| 4,815,449 | 3/1989 | Horowitz .................................... | 600/7 |
| 4,827,493 | 5/1989 | Parsons et al. .......................... | 378/119 |
| 4,861,520 | 8/1989 | van't Hooft et al. ................... | 252/644 |
| 4,881,937 | 11/1989 | van't Hooft et al. ....................... | 600/3 |
| 4,881,938 | 11/1989 | van't Hooft ................................ | 600/3 |
| 4,891,165 | 1/1990 | Suthanthiran ........................... | 252/633 |
| 4,946,435 | 8/1990 | Suthenthiran et al. ..................... | 600/3 |
| 4,969,863 | 11/1990 | van't Hooft et al. ....................... | 600/3 |
| 5,030,194 | 7/1991 | van't Hooft ................................ | 600/3 |
| 5,030,195 | 7/1991 | Nardi ......................................... | 600/7 |
| 5,163,896 | 11/1992 | Suthanthiran et al. ..................... | 600/8 |
| 5,342,283 | 8/1994 | Good .......................................... | 600/8 |
| 5,405,309 | 4/1995 | Carden, Jr. ................................. | 600/3 |
| 5,503,614 | 4/1996 | Liprie ......................................... | 600/7 |
| 5,683,345 | 11/1997 | Waksman et al. .......................... | 600/3 |
| 5,713,828 | 2/1998 | Coniglime .................................. | 600/7 |

OTHER PUBLICATIONS

Daniel, et al., A New, Rapid Safe Method for Local Radiation of Intrathoracic Sites, *The American Surgeon*, 1989, vol. 55, No. 9, pp. 560–562.

Goldberg, et al., In vivo aortic smooth muscle cell (SMC) kinetics: response to irradiation in the rat, *Cell Tissue Kinet*, 1982, vol. 15, No. 6, p. 675.

Hessel, et al., Angiography and Vasa Vasorum Blood Flow After Aortic Dilatation, *Investigative Radiology*, Sep–Oct 1978, p. 404.

Lee, et al, Effects of Laser Irradiation on Cardiac Valves: Technique of Transcatheter In–Vivo Vaporization of Aortic Valve, *Laser Surg. Med.*, 1983, vol. 3, No. 2, pp. 174–175.

Lee, et al., Laser Irradiation of human atherosclerotic obstructive disease; Simultaneous visualization and vaporization achieved by a dual fiberoptic catheter, *American Heart Journal*, 1983, vol. 105, No. 1, pp. 163–164.

Lee, et al., Effects of laser irradiation on cardiac valves: Transcatheter in vivo vaporization of aortic valve, *American Heart Journal*, Feb. 1984, vol. 107, p. 394.

Solomon, et al., An in vivo method for the evaluation of catheter thrombogenicity, *Journal of Biomedical Materials Research*, 1987, vol. 21, pp. 43–57.

Rosch et al., Gianturco Expandable Wire Stents in the Treatment of Superior Vena Cava Syndrome Recurring After Maximum–Tolerance Radiation, *Cancer* (Phila), 1987, vol. 60, No. 6, pp. 1243–1246.

*Primary Examiner*—Jose G. Dees
*Assistant Examiner*—Dameion Jones
*Attorney, Agent, or Firm*—Foley Hoag & Eliot

[57] ABSTRACT

Past techniques utilized wet chemistry to produce a carrier free radioisotope for a seed implant. However, by using the technique of ion implantation, it is possible to physically separate the precursor isotope by magnetic means and further, to physically direct a beam of these isotopically pure atoms and to embed them into a suitable carrier body. Thus, formation of the seed implant may be accomplished using dry techniques, that is, no liquid chemistry. The systems and methods disclosed herein are designed to produce a beam of a single stable isotope using an ion implanter and to further implant this single stable isotope below the surface of a carrier body. After neutron activation, these single stable isotopes will produce the isotopes iodine-125, palladium-103, cesium-131, or ytterbium embedded within the carrier body. Optionally, the carrier body may be encapsulated prior to activating the precursor isotope embedded in the carrier body.

26 Claims, 3 Drawing Sheets

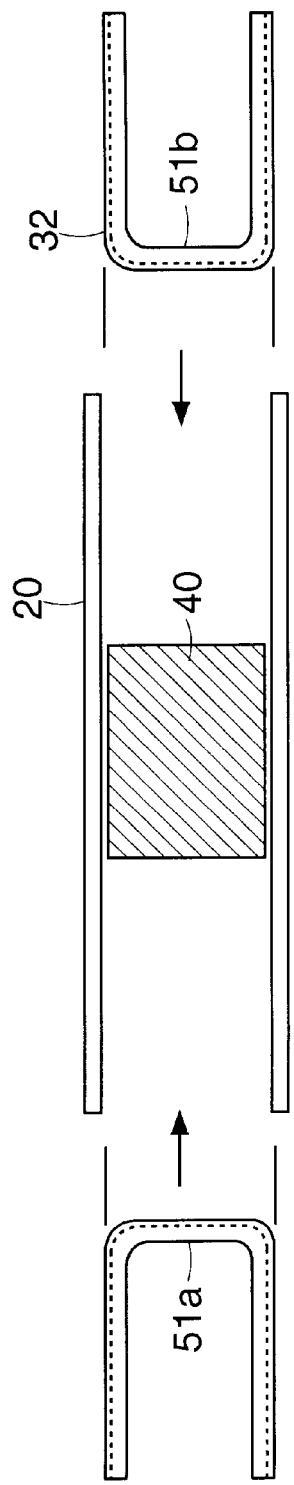
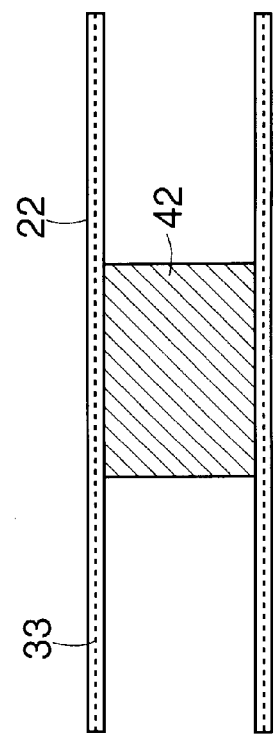
FIG. 4
FIG. 5

RADIOACTIVE SEED IMPLANTS

CROSS-REFERENCE TO RELATED APPLICATION

This application is based on and claims priority to U.S. provisional patent application Ser. No. 60/074,085, entitled "RADIOACTIVE SEED IMPLANTS", filed Feb. 9, 1998, pending.

BACKGROUND

This invention relates to therapeutic radiation oncology and to an improved method of manufacture of radioactive seed implants.

Radioactive pellets or "seeds" have been used to treat cancerous tumors, especially in the prostate gland, for many years. These seeds usually are about 4 mm long and 0.8 mm in diameter and emit low energy x-rays in the 20–40 keV range. The first such source utilized Iodine-125 ($^{125}$I) with a 60-day half life. More recently, Palladium-103 ($^{103}$Pd) with a 17-day half life has been used.

U.S. Pat. No. 3,351,049 to Lawrence discloses a method of impregnating a carrier body with a radioactive liquid containing Iodine-125, Palladium-103, Cesium-131, Xenon-133, or Ytterbium-169. After drying, the carrier body is then encapsulated in a welded canister, e.g., of titanium. Kubiatowitz in U.S. Pat. No. 4,323,055 discloses a method of coating radioactive Iodine-125 on to the surface of specially prepared X-ray detectable rods, e.g., silver rods. These coated silver rods are then encapsulated within a canister, e.g., of titanium, to create a sealed source.

Another method, disclosed by Carden in U.S. Pat. No. 5,405,309 uses cyclotron produced palladium-103 which is electroplated onto one or more pellets of electroconductive material, e.g., graphite rods, and subsequently encapsulated in a shell, such as a welded titanium canister.

Another method disclosed by Coniglione in U.S. Pat. No. 5,713,828 employs a double-walled tubular structure which is hollow along its major axis. This type of construction is stated to reduce the migration of seeds by affording better attachment to tissue. The hollow, double-walled tube also permits a rod of suture material to be placed through the seed for better linear placement of seeds during the clinical procedure.

Coniglione also discloses a non-radioactive pre-seed in which a precursor isotope is plated or otherwise coated onto a substrate prior to neutron activation. This technique cannot produce iodine-125 seeds where the precursor isotope is xenon-124, which, being an inert gas, cannot be plated or otherwise coated onto a substrate. In addition, for a palladium-103 seed the method of Coniglione in fabricating a non-radioactive pre-seed generally requires use of isotopically pure palladium-102 precursor that is electroplated onto a substrate. Natural palladium cannot be used because the presence of palladium-106 would produce a long-lived contaminant radiation which would be unacceptable to the radiation oncologist because it would expose the patient to unwanted gamma radiation. Such high purity enriched palladium-102 must be purchased from, for example, Oak Ridge National Laboratories or other commercial suppliers at high cost. Palladium-102 enriched to 78 atomic percent is available from Oak Ridge at a price of about $868,000 per gram.

In addition, these enriched isotopes cannot be electroplated on non-conductor substrates such as silicon or plastics. Coniglione teaches that these non-conductive substrates must first be metallized prior to plating with the enriched isotope.

All of the above mentioned technologies have the disadvantage that one must work with highly radioactive liquids which takes a high level of skill and is relatively expensive, or use a physical coating or electroplating technique to form the radioactive precursor or radioactive layer on a carrier body.

SUMMARY OF THE INVENTION

Past techniques that used neutron activation to make the radioactive isotopes used very expensive highly enriched isotopes such as palladium-102 or yttrium-89, which were plated on a substrate either before or after activation in a nuclear reactor. In the case of cyclotron-produced radioactively, as taught by Cardon, an extensive chemical separation involving radioactive liquids was required.

These difficulties can be avoided by using the technique of mass-analyzed ion implantation to both separate the desired single isotope from all other isotopes of the element and embed them into the surface of a substrate at extremely high velocity. All of this can be accomplished in one piece of equipment in a common vacuum. In addition, the process uses naturally occurring elements (no enriched isotopes as starting material) and the separated isotope beam can be used to embed these separated isotopes into all materials without regard to whether they are metals, ceramics, or polymers.

A device according to the present invention includes a carrier body in which radioactivity is embedded beneath its surface, and which is then contained inside a sealed titanium cannister or otherwise encapsulated with a titanium coating. A significant aspect of the invention is the use of ion implantation to embed the precursor isotope beneath the surface of the carrier body. The ion implanter used to make the device can use natural elements, such as naturally occurring xenon, palladium, or ytterbium, in its ion source. The ion implanter accelerates the ions of the source element, mass separates the desired single precursor isotope, and embeds the single precursor isotope at high velocity beneath the surface of a carrier body. All of these steps are accomplished in one apparatus and within a common vacuum chamber.

It is an object of this invention to produce a single isotope beam using an ion implanter and to further implant this single isotope below the surface of a carrier body and to later neutron activate the single isotope to form a single radioisotope.

Another object of this invention is to produce isotopically pure radioisotopes embedded in a carrier body for the isotopes consisting of Iodine-125, Palladium-103, Cesium-131, and Ytterbium-169.

It is a further object of this invention to encapsulate the carrier body prior to activating the precursor isotope embedded in the carrier body.

A radioactive seed implant according to the techniques and methods disclosed herein may include at least one carrier body having a surface; and at least one radioactive isotope embedded substantially beneath the surface of the carrier body. The radioisotope may be palladium-103, iodine-125, cesium-131, or ytterbium-169, or may be a combination or thereof. The carrier body may include aluminum, titanium, silicon, silicon dioxide, alumina, copper or rhodium, or some combination or variation thereof. One or more radiopaque pellets or wires may be used in the seed implant so that the location of the implant may be seen by x-ray.

A coating of biocompatible material, e.g., of titanium, carbon, or some combination or variation thereof, may be applied on the surface of the carrier body. The coating of biocompatible material may be between approximately 0.5 microns and approximately 20 microns thick, including all subranges within this range of thickness, depending on the composition of the materials used and the amount of dosage desired for the targeted tissue.

A pre-seed implant according to the techniques and methods described herein, may include at least one carrier body having a surface, and at least one stable isotope ion implanted substantially beneath the surface of the carrier body. A plurality of carrier bodies may be used, if so desired.

The stable isotope for the pre-seed implant may be palladium-102, xenon-124, barium-130, or ytterbium-168, or a combination or variation thereof. The carrier body of the pre-seed implant may include titanium, silicon, silicon dioxide, alumina, copper or rhodium, or some combination or variation thereof, including varying degrees of purity as well as combinations with other materials.

The pre-seed implant may also include one or more radiopaque pellets, which may be formed of a material that does not activate under thermal neutron bombardment, such as rhodium, gallium arsenide, copper, or lead, or some combination or variation thereof.

An alternative form of a radioactive seed implant may include a canister having two ends and an opening at each end, a radiopaque pellet disposed within the canister, a pair of carrier bodies having an inside surface and an outside surface, and at least one radioactive isotope embedded substantially beneath the inside surface of the carrier bodies, wherein the inside surface of each of the carrier bodies is received within each of the openings in the canister.

A non-radioactive pre-seed implant corresponding to the alternative form of radioactive seed implant may include a carrier body having an inside surface and an outside surface, and at least one stable isotope ion implanted substantially beneath the inside surface of the carrier body.

A method of preparing a pre-seed implant may include forming at least one carrier body of a material that does not become substantially radioactive under thermal neutron bombardment, and ion implanting a stable isotope into the surface of the carrier body. Ion implanting the stable isotope may include ion implanting at a dosage between approximately $1 \times 10^{16}$ ions/cm$^2$ and approximately $1 \times 10^{19}$ ions/cm$^2$, as well as all subranges and variations of this dosage. Ion implanting a stable isotope may include ion implanting palladium-102, xenon-124, barium-130, or ytterbium-168, or some combination or variation thereof.

A method of preparing a pre-seed implant may further include applying a coating of biocompatible material on the surface of the carrier body, e.g., by a sputtering process, and may involve applying a coating of biocompatible material to the carrier body during or after ion implantation. Such a method may further include encapsulating one or more of the carrier bodies and a radiopaque pellet within a titanium canister and welding the canister shut.

A method of preparing a radioactive seed implant may include forming at least one carrier body of a material that does not become substantially radioactive under thermal neutron bombardment, ion implanting at least one stable isotope into the surface of the carrier body, and exposing the stable isotope to neutron irradiation produce therapeutic quantities of a radioisotope. Such a method may further include placing the carrier body into a titanium canister, placing at least one pellet of a radiopaque material into the titanium canister, and welding one or more titanium end caps on the titanium canister to form a sealed container. Exposing the stable isotope to neutron irradiation may include thermal neutron activating the stable isotope at a dosage between approximately $1 \times 10^{17}$ neutrons/cm$^2$ and $1 \times 10^{20}$ neutrons/cm$^2$, or between any of the subranges and variations of such dosage. Exposing the stable isotope to neutron irradiation to produce therapeutic quantities of a radioisotope may include neutron activating the sealed container to produce therapeutic quantities palladium-103, iodine-125, cesium-131, or ytterbium-169, or some combination or variation thereof.

A method of treatment of a cancerous tumor according to the techniques and systems disclosed herein may include forming at least one carrier body of a material that does not become substantially radioactive under thermal neutron bombardment, ion implanting at least one stable isotope into the surface of the carrier body, exposing the stable isotope to neutron irradiation produce therapeutic quantities of a radioisotope, placing the carrier body into a canister, placing at least one pellet of a radiopaque material into the canister, and placing the canister in an area of tissue affected by the tumor.

BRIEF DESCRIPTION OF DRAWINGS

FIG. 4 illustrates a further alternative embodiment of a radioactive seed implant where the endcaps also serve as the ion implanted carrier bodies.

FIG. 5 illustrates another alternative embodiment of a radioactive seed implant where a single tube is implanted with the precursor isotope and where there is no need for welding.

DETAILED DESCRIPTION OF THE EMBODIMENTS

Figure 1:
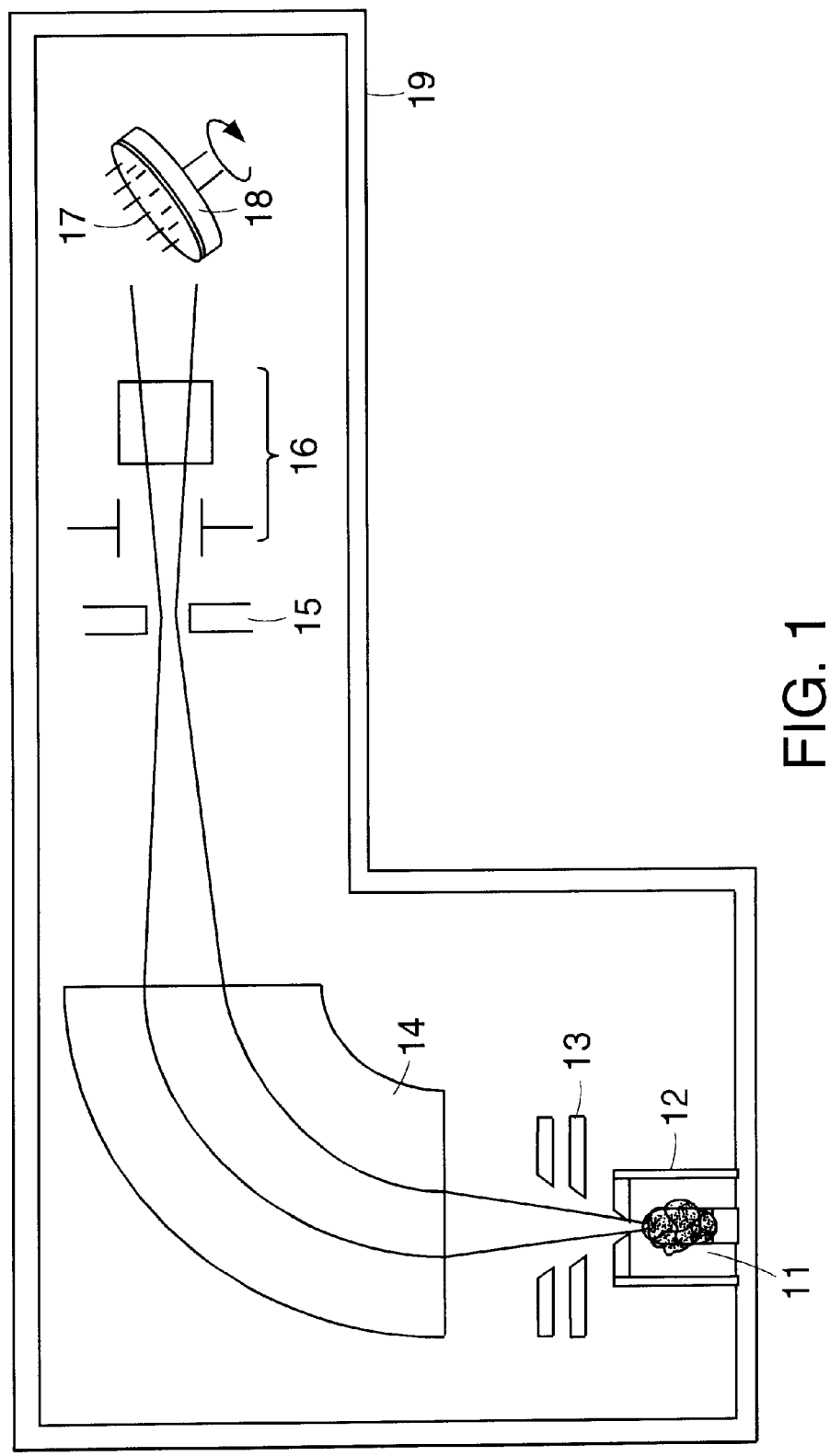
FIG. 1 schematically illustrates a mass-analyzed ion implantation apparatus used to embed the single precursor isotope into the carrier bodies.

FIG. 1 of the drawings illustrates schematically an ion implantation apparatus that can be used to embed single precursor isotopes into carrier bodies for the preferred embodiments of the invention. In this apparatus, a confined plasma 11 of the element containing the specific isotope to be implanted is creates within an ion source 12. The positive ions are extracted by a set of electrodes 13 and accelerated into a mass-analyzing magnet 14. The specific isotope is then focused and passed through a mass selection slit 15. The ion beam is then raster scanned in the horizontal and vertical directions by a set of scanner plates 16 and directed onto an array of carrier bodies 17, which are held on a rotating platform 18. All of the elements of this apparatus are contained within a single vacuum, which is represented by a chamber 19. The ion beam of the separated non-radioactive isotope is typically accelerated to energies up to 200 keV, which can embed these isotope atoms up to 0.2 microns deep into the carrier bodies. The carrier bodies, which are typically cylindrical in shape, are rotated and tilted at a 45° angle to the beam to uniformly implant the outside surfaces and to prevent shadowing of one carrier body by the others.

Ion implantation may be accomplished using a high current ion implanter such as presently widely used in the semiconductor industry for doping silicon electronic devices. For example, Eaton model NV-GSD or Varian model 180XP having beam currents in excess of 20 milliamperes can be used. The ion implanter should have sufficient beam current capability and mass resolution to generate at least a few microamps of the desired light isotope. For example, naturally occurring xenon has nine isotopes ranging in mass from 124 to 136. Xenon-124, however, only has a relative abundance of 0.1%. A ten milliamp capability implanter would yield ten microamps of xenon-124.

Typical beam currents for xenon-124, for example, would therefore be ten to twenty microamps. For a typical array of carrier bodies consisting of 1600 pieces mounted on a three inch diameter plate, the implantation time would be twenty-five to fifty hours per batch.

Figure 2:
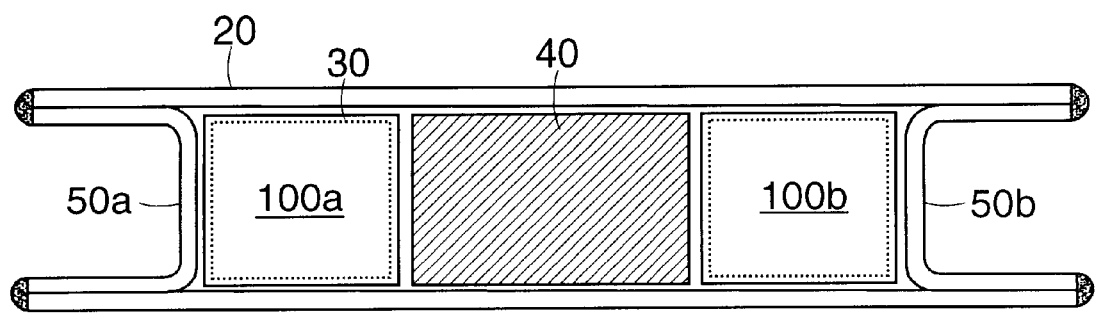
FIG. 2 illustrates a cross-sectional view of a radioactive seed implant according to one embodiment of the present invention where two radioactive seeds are separated by a radiopaque pellet.

FIG. 2 of the drawings illustrates one of the preferred embodiments of the devices and methods disclosed herein. In FIG. 2, two carrier bodies 100a, 100b, at each end of the seed are made of an appropriate low atomic number, low density material, and are surface implanted 30 with the lowest weight isotope of xenon, palladium, barium, or ytterbium using a high current ion implanter. These lowest weight isotopes are xenon-124, palladium-102, barium-130, or ytterbium-168 respectively. Any isotope that can be activated by neutron activation may be ion implanted into the surface.

Preferred isotopes for implantation should be essentially free of alpha and beta emissions after activation, and should have greater than 95% of their radiation in low energy X-rays of energy less than 100 thousand electron volts (keV).

Upon activation, xenon-124 becomes xenon-125 which has a 17.1 hour half-life, and quickly beta decays to iodine-125. Iodine-125 is desirable because it is in widespread use and can be beneficial for the treatment of early stages of prostate cancer. Ytterbium-169 may be useful for both early, middle, and late stages of prostate cancer. Palladium-103 is useful for more advanced stages of prostate cancer or for more aggressive forms of cancer. The usefulness of a radioisotope for a particular type of cancer or a particular stage of cancer is generally related to the half-life of the radioisotope and the total dose.

There will generally be some absorption of the radiation by the encapsulation material 20, and such absorption will tend to diminish the amount of radiation delivered to the tissue to be treated. Thus, the desired radiation dosage amount and the attenuation factor should be considered in determining the quantity and type of isotope to be used. In addition, the amount of absorption generally will be related to the thickness of the capsule walls 20, which preferably should be thick enough to provide sufficient mechanical strength to the seed. Preferably, the capsule material 20 should be selected from low atomic number materials, for example, with an atomic number lying in the range of 4 to 28. The capsule material 20 preferably should be corrosion resistant, compatible with body tissue and nontoxic, or should have a coating with these characteristics.

An appropriate low density, low atomic number carrier body 100a, 100b may be made of single crystal silicon from a semiconductor wafer. Alternatively, the carrier body could be a combination, e.g., a coating of titanium or silicon applied outside a silica or alumina substrate.

Single crystal semiconductor grade silicon is a preferred material because it does not contain contaminants that will activate significantly in a nuclear reactor. Semiconductor grade silicon is one of the purest substances made by man, containing less than one part per billion of neutron activatable elements. In an appropriate vacuum chamber, the isotopically pure ion beam is directed on the silicon carrier body using a kinetic energy of approximately twenty to approximately 200 keV for such a duration as to ion implant between approximately $1\times10^{17}$ to approximately $1\times10^{18}$ ions/cm$^2$ on substantially all surfaces of the pellet. At 200 keV, the ions will penetrate up to approximately 2,000 angstroms into the silicon surface.

After implantation, the pellets are placed in a high flux nuclear reactor, such as the University of Missouri Research Reactor, at a flux rate of approximately $8\times10^{13}$ neutrons/cm$^2$/sec.

After activation, two pellets 100a, 100b, and a lead, gold, or tungsten pellet 40, are placed in a titanium tube 20, with a pair of end caps 50a, 50b, as shown in FIG. 2, and the end caps are laser welded to form a sealed "seed". The seal of the seed is designed to prevent migration of the radioisotope and preferably should not have radiation shielding properties. Optionally, the tube could be made from titanium combined with another material, e.g., aluminum, but this could be somewhat difficult to weld.

In the preceding case, only the silicon carrier bodies 100a, 100b, were placed in the reactor and consequently, the assembly and laser welding must be done while the assembly is radioactive.

Alternately, if sufficiently pure titanium and radiopaque marker material can be manufactured, it is possible to load-up and weld the assembly together before placing the assembly in the nuclear reactor for activation. Titanium is preferred for encapsulation because it is one of the most biocompatible materials available and, following activation, it does not contain a significant quantity of radioisotopes with long half-lives. Moreover, titanium may be obtained in very pure form, e.g., of 99.999% purity. Care must be taken however to make sure that any remaining impurities do not activate to long half-life radioisotopes.

Figure 3:
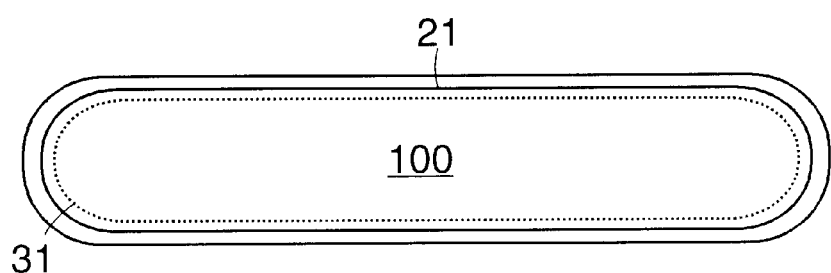
FIG. 3 illustrates an alternative embodiment of a radioactive seed implant using a single ion implanted carrier body which is coated with a sealant metal.

Referring to FIG. 3, this alternate approach uses a carrier body 100 made of ultra pure copper, rhodium, or other high atomic number, high density element or compound which does not produce a significant quantity of long lived radioisotopes under neutron bombardment. Copper, for example, has two stable isotopes, $^{63}$Cu and $^{64}$Cu which neutron activate to $^{64}$Cu and $^{66}$Cu respectively. These two radioisotopes have half-lives of twelve hours and five minutes respectively and will decay to zero before the seed is implanted into a patient. Similarly rhodium has no long lived neutron capture products. Whatever carrier material is used, it should be possible to fabricate the material in the small dimensions desired for the seed implant.

Copper also is desirable because it is available in purities of 99.999% (Alpha Chemicals) and in wire form. Care must be taken however to make sure that the remaining impurities do not activate to long half-life radioisotopes. Iron, cobalt, zinc, and manganese contaminants preferably should be avoided. Similarly the metal rhodium preferably should be free of platinum and iridium contaminants.

A sufficiently pure carrier body 100 would be ion implanted with one of the four aforementioned pure isotopes 31 to a dose of approximately $1\times10^{16}$ to approximately $1\times10^{18}$ atoms/cm$^2$. In this case, there should preferably be a simultaneous deposition of titanium on the carrier body 100 to lower the sputtering rate of the carrier body material due to the impingement of the ion beam. Alternatively, one could alternate the ion implant and titanium sputter coating, for example, for approximately five times, while implanting the full required dose. After ion implantation, the seed could be sputter coated with ultra pure titanium 21, to a thickness of approximately ten microns to approximately twenty microns, using magnetron sputtering to further encapsulate the seed, although this may not be necessary.

The assembly would then be placed in a nuclear reactor to produce the required radioactivity.

The shape of the radioactive seed implant preferably is rounded so that the radiation distribution is spherical off each end, thereby making the implant more similar to a uniform point source. However, there are difficulties in machining a rounded shape for such a small diameter object, so a different shape, such as a more square shape, may be used instead.

FIG. 4 shows an exploded view of an additional alternate embodiment in which two end caps 51a, 51b are also the carrier bodies for the ion implanted isotope 32. When the two end caps 51a, 51b are inserted and welded, they also serve to center and pin the radiopaque marker 40 in place within the tube 20.

FIG. 5 shows still another alternate embodiment where a single titanium tube is used as a carrier body 22. The stable precursor isotope 33 is ion implanted into the surface of the carrier body 22 which can then simultaneously, or after ion implantation, be sputter coated with pure titanium to provide additional sealant for the radioactivity after the carrier body is activated in a nuclear reactor. After activation, a radiopaque pellet 42 may be placed in the center of the tube. Since the radiopaque pellet is placed in the tube after activation, it need not be made of a non-activatable material and is preferably made of gold. Using gold, for example, the pellet may be squeezed from both flat sides to cause it to bulge radially and thus be substantially permanently jammed into the tube.

This embodiment most clearly illustrates the advantages of ion implantation of the precursor isotope over other methods of coating, such as electroplating or physical vapor deposition. With ion implantation, there is no need for a double-walled tube to encapsulate the radioisotope, such as taught by Coniglione. A hollow tube structure can be made and sealed using a single tube construction.

The following examples are included to further illustrate the invention for three specific radioisotopes, but are to be considered as exemplary only and not as limiting the invention in any way.

EXAMPLE #1

The following example illustrates the process of making a radioactive seed containing $^{125}$I according to the embodiment of FIG. 3.

carrier body: 99.999% pure copper size: 0.75 mm dia., 4 mm long, spherical ends surface area: 0.08 cm$^2$ $^{124}$Xe implant dose: $1\times10^{17}$ atoms/cm$^2$ ion implant energy: 200 keV $^{124}$Xe atoms in surface: $8\times10^{15}$ atoms sputter coat of titanium: 1 micron thick neutron dose rate: $8\times10^{13}$ neutrons/cm$^2$/sec neutron dose duration: 290 hrs initial $^{125}$I activity: 0.4 millicurie photon equiv. activity: 0.6 millicurie Eighteen days after removal from the nuclear reactor, which allows adequate time for total radioactivity measurement, certification, and sterilization, the seed will have decayed to 0.5 millicurie and will be ready to implant into a diseased prostate gland. At a 0.5 millicurie source strength, approximately 160 Grays absorbed dose will be given to the tumor surrounding an array of 80 to 100 seeds properly spaced within the prostate gland.

EXAMPLE #2

The following example illustrates the process of making a radioactive seed containing $^{103}$Pd according to the embodiment of FIG. 5.

carrier body: 99.999% pure titanium tube size: 0.81 mm dia., 4.5 mm long surface area: 0.115 cm$^2$ $^{102}$Pd implant dose: $2\times10^{18}$/cm$^2$ ion implant energy: 200 keV $^{102}$Pd atoms in surface: $2.30\times10^{17}$ sputter coat of titanium: 1 micron thick neutron dose rate: $8\times10^{13}$ neutrons/cm$^2$/sec neutron dose duration: 522 hrs initial $^{103}$Pd activity: 1.3 mCi photon equiv. activity: 1.0 mCi One millicurie of $^{103}$Pd will produce approximately 160 Grays at a tumor site.

EXAMPLE #3

The following example illustrates the process of making a radioactive seed implant containing $^{169}$Yb according to an embodiment of FIG. 2.

carrier bodies: semiconductor silicon (2 pieces)

size: 0.6 mm×0.6 mm×1 mm long each surface area: 0.048 cm$^2$ (for 2 pieces)

$^{168}$Yb implant dose: $1\times10^{16}$/cm$^2$ ion implant energy: 200 keV $^{168}$Yb atoms on surface: $1.15\times10^{15}$ sputter coat of titanium: 1 micron thick neutron dose rate: $8\times10^{13}$ neutrons/cm$^2$/sec neutron dose duration: 143 hrs Initial $^{169}$Yb activity: 0.5 mCi photon equiv. activity: 1.1 mCi (between 50–63 keV x-rays)

At this seed activity, the dose at the tumor site is approximately the correct therapeutic dose of 160 Grays for an array of 80–100 seeds.

While the invention has been disclosed in connection with the preferred embodiments shown and described in detail, various modifications and improvements will be apparent to one of ordinary skill in the art from the above description. For example, and without limitation, it may be beneficial to ion implant two or more different stable isotopes prior to activation. For example, it may be useful to combine equal proportions of ytterbium and iodine, thereby yielding a higher radiation dose to the patient in the short term, then leveling off to a slower dose rate in the longer term. The proportion of each isotope used could be determined based on the therapeutic effects desired for the patient.

I claim:

1. A pre-seed implant, comprising:
   at least one carrier body having a surface; and
   at least one stable isotope selected from palladium-102, xenon-124, barium-130, and ytterbium-168 ion-implanted substantially beneath the surface of said carrier body.

2. The pre-seed implant of claim 1, wherein said carrier body includes a material selected from aluminum, titanium, silicon, silicon dioxide, alumina, copper and rhodium.

3. The pre-seed implant of claim 1, further comprising a radiopaque pellet formed of a material that does not substantially activate under thermal neutron bombardment.

4. The pre-seed implant of claim 1, further comprising a radiopaque pellet including at least one material selected from rhodium, lead, and copper.

5. The pre-seed implant of claim 3, further comprising a canister surrounding said radiopaque pellet and said carrier body.

6. The pre-seed implant of claim 5, wherein said canister comprises at least one material selected from titanium, silicon, and carbon.

7. A pre-seed implant, comprising:

at least one carrier body having a surface; and at least one stable isotope selected from xenon-124, barium-130, and ytterbium-168, said isotope being embedded substantially beneath the surface of said carrier body.

8. The pre-seed implant of claim 7, wherein said carrier body includes a material selected from aluminum, titanium, silicon, silicon dioxide, alumina, copper and rhodium.

9. The pre-seed implant of claim 7, further comprising a radiopaque pellet formed of a material that does not activate under thermal neutron bombardment.

10. The pre-seed implant of claim 7, further comprising a radiopaque pellet including at least one material selected from rhodium, lead, and copper.

11. The pre-seed implant of claim 10, further comprising a canister surrounding said radiopaque pellet and said-carrier body.

12. The pre-seed implant of claim 11, wherein said canister comprises at least one material selected from titanium, silicon, and carbon.

13. A method for activating a pre-seed implant, comprising providing a pre-seed implant comprising a carrier body having at least one stable isotope selected from palladium-102, xenon-124, barium-130, and ytterbium-168, said isotope being ion-implanted substantially beneath the surface of said carrier body, and exposing said pre-seed implant to a flux of thermal neutrons.

14. A method for activating a pre-seed implant, comprising providing a pre-seed implant comprising a carrier body having at least one stable isotope selected from xenon-124, barium-130, and ytterbium-168, said isotope being embedded substantially beneath the surface of said carrier body, and exposing said pre-seed implant to a flux of thermal neutrons.

15. A pre-seed implant prepared by a method comprising providing a carrier body, and incorporating into the carrier body by ion implantation a stable isotope selected from palladium-102, xenon-124, barium-130, and ytterbium-168.

16. The pre-seed implant of claim 15, wherein said carrier body includes a material selected from aluminum, titanium, silicon, silicon dioxide, alumina, copper, and rhodium.

17. The pre-seed implant of claim 15, further comprising a radiopaque pellet formed of a material that does not activate under thermal neutron bombardment.

18. The pre-seed implant of claim 15, further comprising a radiopaque pellet including at least one material selected from rhodium, lead, and copper.

19. The pre-seed implant of claim 18, further comprising a canister surrounding said radiopaque pellet and said carrier body.

20. The pre-seed implant of claim 19, wherein said canister comprises at least one material selected from titanium, silicon, and carbon.

21. A radioactive pre-seed implant prepared by a method comprising providing a carrier body, and incorporating into the carrier body by ion implantation a stable isotope selected from palladium-102, xenon-124, barium-130, and ytterbium-168, and exposing said carrier body to a flux of thermal neutrons.

22. The pre-seed implant of claim 21, wherein said carrier body includes a material selected from aluminum, titanium, silicon, silicon dioxide, alumina, copper and rhodium.

23. The pre-seed implant of claim 21, further comprising a radiopaque pellet formed of a material that does not activate under thermal neutron bombardment.

24. The pre-seed implant of claim 21, further comprising a radiopaque pellet including at least one material selected, from rhodium, lead, and copper.

25. The pre-seed implant of claim 24, further comprising a canister surrounding said radiopaque pellet and said carrier body.

26. The pre-seed implant of claim 25, wherein said canister comprises at least one material selected from titanium, silicon, and carbon.

\* \* \* \* \*